United States Patent [19]
Childers et al.

[11] Patent Number: 5,837,193
[45] Date of Patent: Nov. 17, 1998

[54] METHOD OF DECONTAMINATING FREEZE DRYERS

[75] Inventors: Robert Warren Childers, Garner; Columbus Clark Cockerham, Jr., Apex; Matthew Stuart Dixon, Raleigh, all of N.C.; John William Johnson, Vicksburg, Mich.; Thaddeus J. Mielnik, Apex, N.C.; Manfred Michael Steiner, Hurth, Germany

[73] Assignee: American Sterilizer Company, Erie, Pa.

[21] Appl. No.: 450,931

[22] Filed: May 24, 1995

Related U.S. Application Data

[63] Continuation of Ser. No. 973,371, Nov. 12, 1992, abandoned.

[51] Int. Cl.⁶ .................................................. A61L 7/00
[52] U.S. Cl. ........................ 422/28; 34/92; 422/31; 422/33; 422/34; 422/292; 422/295; 422/298
[58] Field of Search .......................... 422/1, 28, 31, 422/33, 34, 292, 295, 298, 305, 307; 34/92

[56] References Cited

U.S. PATENT DOCUMENTS

| | | | |
|---|---|---|---|
| 3,795,986 | 3/1974 | Sutherland | 34/92 |
| 4,169,123 | 9/1979 | Moore | 422/29 |
| 4,230,663 | 10/1980 | Forstrom | 422/33 |
| 4,512,951 | 4/1985 | Koubeck | 422/28 |
| 4,642,165 | 2/1987 | Bier | 203/12 |
| 4,744,951 | 5/1988 | Cummings | 422/28 |
| 4,863,688 | 9/1989 | Schmidt | 422/28 |
| 4,909,999 | 3/1990 | Cummings | 422/298 |
| 4,941,519 | 7/1990 | Sastak | 422/28 |
| 4,952,370 | 8/1990 | Cummings | 422/28 |
| 4,956,145 | 9/1990 | Cummings | 422/28 |
| 4,961,273 | 10/1990 | Fay | 34/92 |
| 5,068,087 | 11/1991 | Childers | 422/26 |
| 5,286,448 | 2/1994 | Childers | 422/28 |
| 5,389,336 | 2/1995 | Childers | 422/28 |

FOREIGN PATENT DOCUMENTS

| | | |
|---|---|---|
| WO A 91 07193 | 5/1991 | WIPO . |
| WO A 92 15337 | 9/1992 | WIPO . |
| WO A 93 17726 | 9/1993 | WIPO . |

OTHER PUBLICATIONS

R.F. Ryan, Operational Control and Optimization of Lyophilization Cycles and Equipment, Jun. 1992.
Brian Vaz, "Dynamic Vapor Penetration of Sterilizing Mixtures", 1985.
Johnson, "Vaporized Hydrogen Peroxide Sterilization of Freeze Dryers", Oct. 1991.
"Lyophilizer Operational Qualification", date prior to 1992, Leybold–Haraeus.
Graham, "Sterilization of Isolators and Lyophilizers with Hydrogen Peroxide in the Vapor Phase", Feb. 1992.

*Primary Examiner*—Robert J. Warden
*Assistant Examiner*—Krisanne M. Thornton
*Attorney, Agent, or Firm*—Fay, Sharpe, Beall, Fagan, Minnich & Mckee

[57] ABSTRACT

A method of decontaminating or sterilizing freeze dryers at low temperature and pressure levels by utilizing sterilant vapor is disclosed.

15 Claims, 2 Drawing Sheets

METHOD OF DECONTAMINATING FREEZE DRYERS

This application is a continuation of U.S. patent application, Ser. No. 07/973,371 filed Nov. 12, 1992 now abandoned.

FIELD OF INVENTION

The present invention relates to a method for decontaminating freeze dryers. More particularly, the invention relates to a method of sterilizing a freeze dryer with sterilant vapor.

BACKGROUND OF THE INVENTION

Freeze dryers used in the pharmaceutical and other industries traditionally include a freeze dryer chamber, shelves in the chamber for holding the product(s) to be freeze dried, a condenser with refrigerator coils, a vacuum system, and piping for connecting the freeze dryer components. Generally, the freeze dryer shelves are heated and cooled during the freeze drying cycle with heating and cooling means, such as a heat transfer fluid circulating through the shelves and a heat exchanger.

Typically, the products to be freeze dried are in loosely capped containers, which are then placed on the freeze dryer shelves. After the chamber door is closed, the shelves are cooled to about −40° C. to freeze the product. Thermocouples, or other temperature probes, indicate when the product is frozen and at the correct temperature. The freeze dryer chamber and condenser are then evacuated through a top, side or rear port on the condenser to a deep vacuum of about 200 microns of Hg (1 Torr=1000 micron of Hg=1 mm of Hg) while the condenser coils are cooled to around −40° C. As sublimation of moisture from the product occurs, it cools the product further. The shelves are warmed to maintain the frozen product at the desired temperature.

The vaporous moisture from the product escapes from the loosely capped containers and is drawn in vapor form from the containers in the chamber to the condenser. In the condenser, the vapor condenses and then freezes on the condenser coils.

This process continues until the product is sufficiently freeze dried as determined by known means. The chamber is vented to atmospheric pressure, the containers are capped (if it is desired), the chamber door is opened, and the freeze dried product removed.

Traditionally, the condenser is defrosted before the next freeze drying cycle using water or steam. The water or steam may be flowed through the condenser or it may be used to flood the condenser. The chamber is typically isolated from the condenser during this process by a large butterfly or mushroom valve. The condenser is drained at the end of the defrost. The chamber is typically Cleaned In Place (C.I.P.) either manually or automatically between each load to remove any debris from the previous load.

Decontamination and sterilization are currently accomplished using formaldehyde vapor, ethylene oxide gas, peracetic acid, liquid hydrogen peroxide, or steam. Each of these methods presents serious disadvantages. For the purposes of this invention the term decontamination means a 3 log (or greater) reduction in bioburden and sterilization means a 6 log (or greater) reduction in bioburden.

Methods using formaldehyde vapor and ethylene oxide gas typically operate at pressures below 15 psig and at temperatures below 140° F.; however, the sterilizing agents are undesirable because they are considered carcinogenic and may be harmful to the operator. Residual removal is also a problem. Ammonia is used to neutralize the formaldehyde gas, leaving a white powder distributed throughout the freeze dryer which is difficult to remove without compromising sterility.

Ethylene oxide vapors can be removed and catalyzed during a lengthy aeration (i.e. more than 8 hours); however, various air/ethylene oxide mixtures which are present during the decontamination/sterilization process are explosive. Consequently, ethylene oxide is typically mixed with Freon 12, an ozone depletor which must be recovered at great expense.

Peracetic acid and liquid hydrogen peroxide may also be sprayed manually, or automatically, throughout the interior of freeze dryers. This method, though, is ineffective on inaccessible areas such as the condenser and "dead legs" (dead-ended piping or lumens) in the freeze dryer unit. Completely flooding the freeze dryer is also not effective since air pockets will prevent the liquid from penetrating into many of the same inaccessible areas.

Steam is emerging as the method of choice. Steam sterilization, however, is achieved at very high temperatures and pressures. As a result, this method requires that the freeze dryer chamber, condenser and associated piping be subjected to high temperature and pressure. The combined high pressure and temperature of steam sterilization (e.g., 250° F. and 15 psig) when alternated with freeze drying while deeply evacuated (at −40° F. and at approximately 200 microns of Hg absolute) takes its toll on the reliability of the freeze dryer system. Furthermore, existing freeze dryers which do not meet the required temperature/pressure requirements cannot be retrofit for steam decontamination/sterilization.

There is a need for a method which can decontaminate or sterilize freeze dryers at low temperatures and at, or below, atmospheric pressure. There is a further need for a method for decontaminating or sterilizing freeze dryers, that can be economically retrofitted onto existing freeze dryers. There is also a need for a method for decontaminating or sterilizing freeze dryers, without using hazardous sterilants or chemicals having hazardous decomposition products which are harmful to the environment.

SUMMARY OF INVENTION

It is therefore a main object of the present invention to provide a method of effectively decontaminating, and preferably sterilizing, freeze dryers at low temperature and pressure levels without using hazardous sterilants or chemicals having hazardous decomposition products.

Additional objects and advantages of the invention will be set forth in part in the description which follows, and in part will be obvious from the description, or may be learned by practice of the invention. The objects and advantages of the invention may be realized and obtained by means of instrumentalities and combinations particularly pointed out in the appended claims.

To achieve these objects and in accordance with the purpose of the invention, the present invention provides a method of decontaminating, preferably sterilizing, a freeze dryer system with sterilant vapor, at the completion of freeze drying cycle, wherein the freeze dryer comprises a freeze dryer chamber and a condenser, which are fluidly coupled to each other and to the source of sterilant vapor. Actual decontamination/sterilization is accomplished by deeply evacuating the freeze dryer components and then introducing vaporized sterilant and exposing the interior surfaces of the freeze dryer components to the vapor for a period of time sufficient to achieve a predetermined level of decontamination.

The method includes the steps of warming the freeze dryer chamber and condenser for a period of time sufficient to bring their temperature to between about 40 to about 60° C., drying the warm chamber and condenser for a period of time sufficient to remove substantially all moisture from the chamber and condenser, cooling the chamber and condenser for a period of time sufficient to bring their temperature to between about 10° and about 40° C., and exposing the chamber and condenser at a temperature between 10° C. and about 40° C. to sterilant vapor and at subatmospheric conditions for a period of time sufficient to achieve a predetermined level of decontamination.

The sterilant vapor preferably contains hydrogen peroxide vapor and more preferably consists of hydrogen peroxide vapor and water vapor.

During the exposing step, the temperature distribution within the chamber and condenser is preferably maintained to within plus and minus about three degrees of a nominal temperature ranging about 10° C. to about 40° C., preferably 30° C. The pressure preferably ranges from between 200 microns to about 200 Torr.

Warming the chamber and condenser preferably comprises heating the floors of the chamber and condenser, and more preferably, also the chamber shelves and walls as well as the condenser walls.

The method may also comprise the steps of isolating the condenser from the chamber, defrosting the condenser, and draining the condenser, prior to the drying step. The method may further comprise the step of rinsing the chamber with water, and draining the chamber through a drain line fluidly coupled to the chamber, prior to the drying step.

The method may also comprise the step of aerating the chamber after decontamination, to remove substantially all sterilant vapor from the chamber and condenser.

DETAILED DESCRIPTION OF THE PREFERRED EMBODIMENT

The present invention provides a method for decontaminating and/or sterilizing a freeze dryer using a sterilant vapor at low temperature, i.e., less than about 60 degrees C, and at low pressure, i.e., at or below atmospheric pressure. Because the freeze dryer does not need to be designed to withstand high temperatures and pressures, or extreme pressure/temperature swings, the manufacturing costs can be reduced. Further, the method permits retrofitting onto existing freeze dryers, which have not been rated for high pressures and temperatures, with cost savings to the end user.

The sterilant vapor preferably contains hydrogen peroxide vapor, and more preferably consists of hydrogen peroxide vapor and water vapor. Any other sterilant vapor, which achieves the desired level of decontamination at the pressure, temperature and humidity conditions employed in the method, can also be used. Preferably, the level of decontamination reached by practicing the method is sterilization. The sterilant vapor is preferably one which is not hazardous to the operator or the environment, or which readily decomposes to nonhazardous materials. Hydrogen peroxide, for instance, degrades into water vapor and oxygen, which may be released to the environment.

BRIEF DESCRIPTION OF THE DRAWINGS

The present invention can best be understood by reference to the drawings, in which.

DETAILED DESCRIPTION OF THE DRAWINGS

FIGS. 1, 2, 4, and 5

Figure 3:
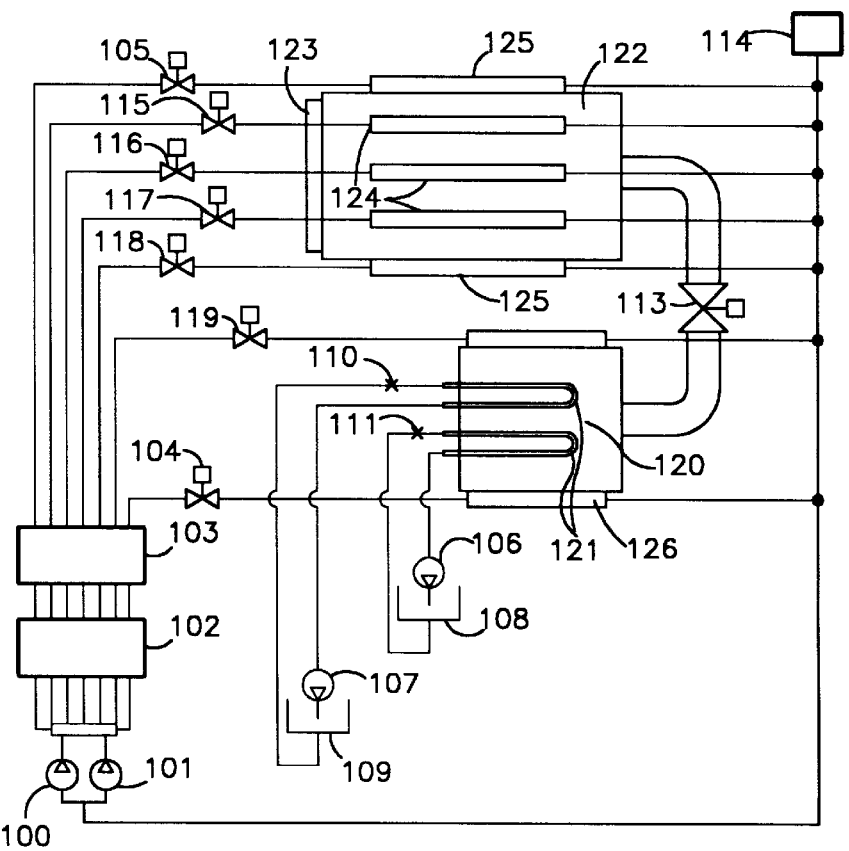
FIG. 3 is a schematic diagram of an alternative heating/cooling system for use in practicing the method of the present invention.

The invention will first be described in reference to FIGS. 1 and 2, which illustrate components of a system for practising a preferred embodiment of the invention, using vapor phase hydrogen peroxide, at the end of the freeze drying cycle, when the condenser is loaded with ice and the entire freeze dryer is cold. Typically, at the completion of the lyophilization cycle, the condenser coils are covered with ice, and the chamber shelves and product are at about 20° C. FIGS. 2 and 3 in "Operational Control and Optimization of Lyophilization Cycles and Equipment" by R. F. Ryan contains temperature profiles for two types of lyophilization cycles. The final chamber pressures for these two typical cycles are 80 microns and 150 microns. At these pressures, water would have to be colder than −42° C. and −37° C., respectively, if it were in the solid (frozen) state.

Figure 1:
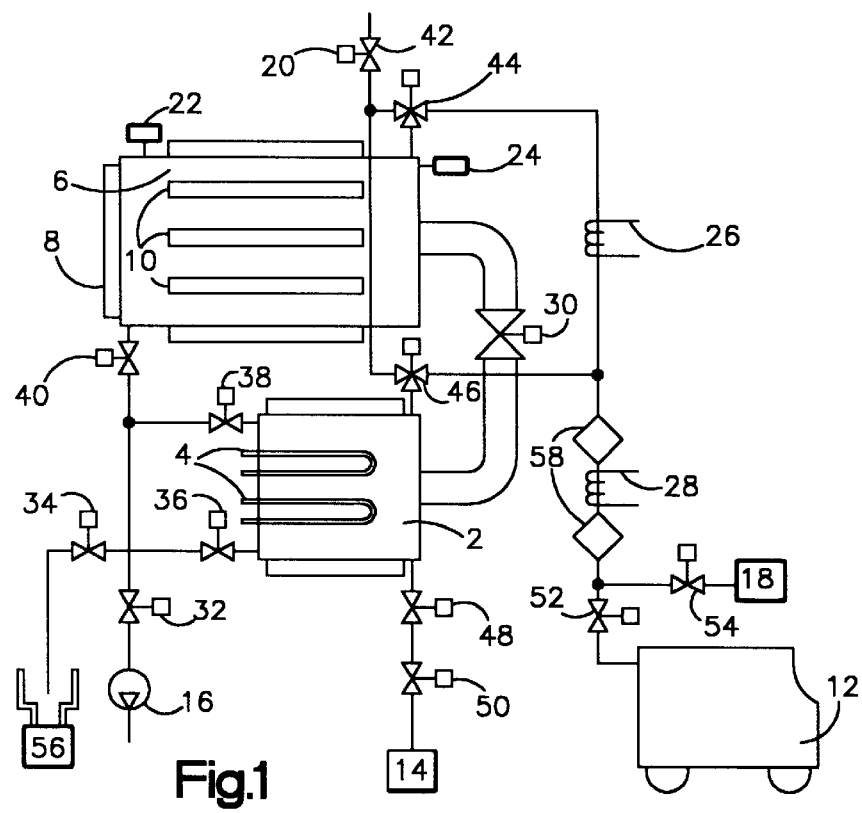
FIG. 1 is a schematic diagram of one embodiment of a system for practicing the method of the present invention.
Figure 2:
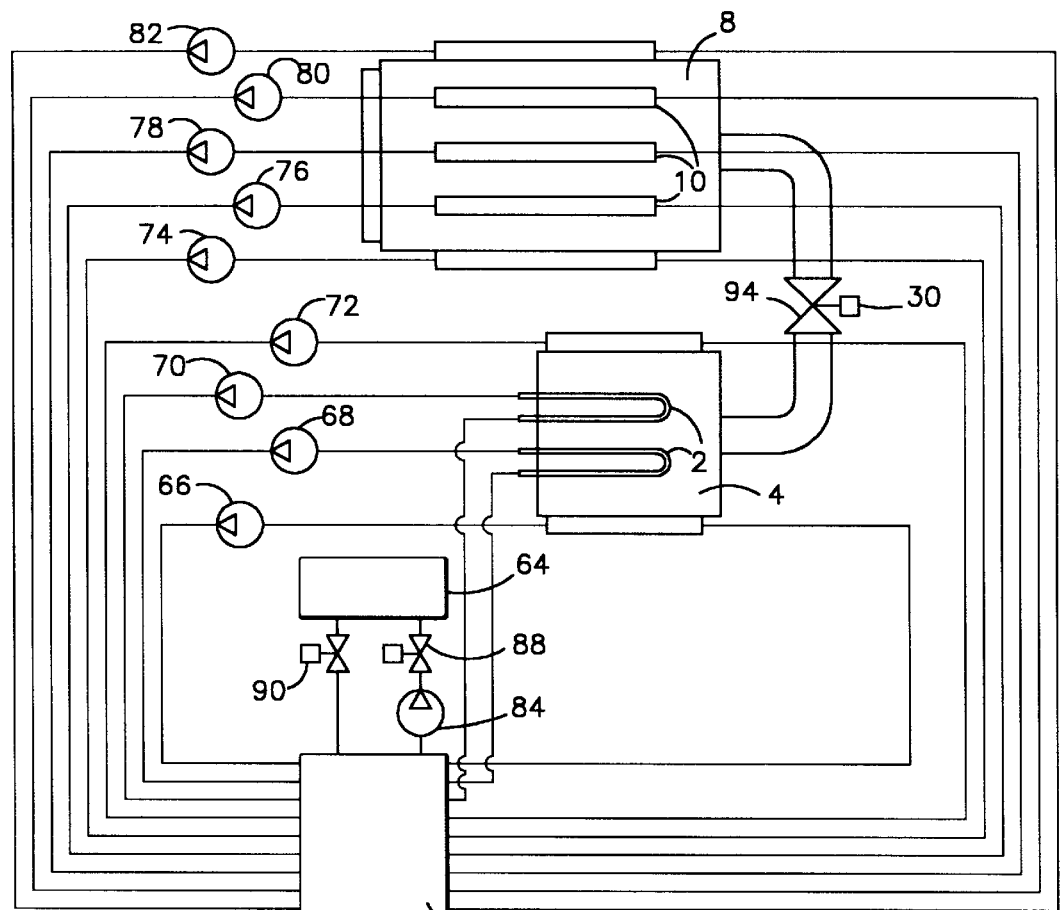
FIG. 2 is a schematic diagram illustrating heating/cooling equipment and associated pumping for use in the system shown in FIG. 1.

The system, as depicted in FIG. 1, includes a condenser 2, refrigerator coils 4 for cooling the condenser 2, a chamber 6 having an access door 8 and shelves 10, and a source of hydrogen peroxide vapor or generator 12. The condenser 2 and the chamber 6 are fluidly coupled to each other and to the generator 12, via suitable conduit, and also to a drain 56, via drain lines. The system also includes a steam supply 14, a vacuum pump 16, a source of vent gas 18, a water supply 20, pressure transducers 22 and 24, heaters 26 and 28, main valve 30, and valves 32, 34, 36, 38, 40, 42, 44, 46, 48, 50, 52, and 54 and air filters 58.

FIG. 2 illustrates additional components for circulating a heat transfer fluid in the chamber and condenser, to heat and cool and control the temperature of the chamber and condenser, while carrying out steps of the invention. In particular, FIG. 2 further depicts a heat exchanger 60, a cold "sink" 62, a heat source 64, pumps 66, 68, 70, 72, 74, 76, 78, 80, 82, 84, and 86, and valves 88, 90, 92, and 94, which are fluidly connected in the system as shown in FIG. 2 via suitable conduit.

The heat transfer fluid is preferably highly compatible with hydrogen peroxide vapor. Thus, if a leak should occur and spray fluid into the evacuated chamber containing hydrogen peroxide, prior to aeration, the potential for hazardous fires or explosions will be avoided. The heat transfer fluid does not need to be compatible with the high temperature requirements associated with steam sterilization.

The heat transfer fluid preferably circulates through and controls the temperature of the floors of the chamber and condenser, during steps of the invention. More preferably, the shelves 10 and the refrigerator coils 4 are also temperature controlled, by circulating the heat transfer fluid there through. It is contemplated that other heating/cooling means can be used to control the temperature of the chamber (including the shelves) and condenser, in the method of the invention. Also, the sidewalls, including the chamber door, and tops of the condenser and chamber can also be temperature controlled.

The sterilant delivery lines connecting the generator 12 to the chamber 6 and condenser 2 are insulated and controllably heated with heaters 28 and 26 to a temperature high enough to prevent the hydrogen peroxide vapors from condensing in the delivery lines, and thereby not reaching the chamber 6 and condenser 2. Excessive temperatures are to be avoided when heating the delivery lines. Preferably, the sterilant delivery lines are controllably heated to about 50° C.

The condenser 2 is isolated from the chamber 6 by closing main valve 30, and is then defrosted. In FIGS. 1 and 2 this can be accomplished by flooding the condenser 2 with water, preferably at about 50° C. through valve 46, for a period of time sufficient to melt substantially all ice in the condenser 2. Preferably, to obtain quicker melting, defrosting also comprises controllably admitting steam through valves 48 and 50, to maintain the temperature of the water in the condenser 2, at the same time that substantially all ice in the condenser 2 is melting. Hot water could alternately be allowed to flow through the condenser and out the drain 56 in a controlled manner during defrost. This would consume a higher quantity of water but would be an effective means to defrost the condenser 2.

It is contemplated that other means for defrosting the condenser 2 can be employed. For instance, steam alone can be injected into the condenser 2. Steam defrosting is not preferred, however, because it is less uniform and leads to hot spots on the freeze dryer surfaces, thereby rendering the subsequent vapor phase sterilization exposure less effective.

If desired, defrosting can be combined with a water spraying of the chamber surfaces and shelves. Known systems for carrying out such water spraying are referred to as "clean-in-place" or C.I.P. systems.

Valves 88 and 90 are opened after or concurrent with the defrost phase, and pumps 66, 68, 70, 72, 74, 76, 78, 80, 82, and 84 are controllably operated for a time period sufficient to warm the chamber 6, shelves 10, condenser 2, and condenser coils 4 to a nominal temperature between about 40° C. to about 60° C., and preferably to about 50° C. Heaters 26 and 28 heat the sterilant delivery lines to about 50° C.

Then, valves 34 and 36 are opened to permit the water in the condenser 2 to flow into the drain 56. When the chamber 6 has been cleaned-in-place with water spraying, or water has otherwise entered the chamber 6, valve 40 is also opened to permit such water to flow into drain 56. The drain lines are ported to the bottoms of the chamber 6 and condenser 2, and slanted so as to allow for gravity drainage into the drain 56.

Next, the warm chamber 6 and condenser 2 are dried for a period of time sufficient to remove substantially all remaining moisture in the chamber 6 and condenser 2. During drying, the chamber 6 and condenser 2 are preferably heated, preferably to between about 40° C. to about 60° C.

The vacuum pump 16 is connected to the drain lines ported at the bottoms of the condenser 2 and the chamber 6, in addition to a top, side, or rear port traditionally used to obtain a deep vacuum during freeze drying. Consequently, the vacuum pump employed should be capable of pumping water vapor and small quantities of liquid with no significant adverse affects on vacuum pump performance. The valving incorporated in the system, namely valves 40 and 32, separately connects the condenser 2 and chamber 6 drain ports to the vacuum, thereby permitting the vacuum to be drawn into and through the vacuum system 16 and exhausted by alternately drawing a vacuum on said lines.

Vacuum system 16 may consist of one, or more, vacuum pumps at least one of which is not adversely affected by water and water vapor. Multiple pumps may be sequenced to operate at different vacuum levels.

In FIGS. 1 and 2, drying begins by sequentially opening valves 40 and 36, when vacuum system 16 is operating, and valves 32, 54, 46, and 44 are open. Filtered vent gas (e.g., air) and moisture are withdrawn through the drain lines.

To ensure complete drying, prior to cooling and sterilant vapor exposure, a deep vacuum is preferably drawn in the condenser 2 and chamber 6, thereby evaporating substantially all remaining moisture in the freeze dryer. The floors of the chamber and condenser are heated to prevent the evaporative cooling from freezing the water that is still remaining during the evaporative drying process. In the embodiment shown in FIGS. 1 and 2, valves 40, 36, and 54 close, valve 38 is opened, and the chamber 8 and condenser 2 are deeply evacuated to less than about 10 Torr. The deep vacuum is applied until substantially all remaining water in the freeze dryer system evaporates and is pulled into vacuum system 16 and exhausted. The deep vacuum may be alternated with vacuum breaks, by admitting vent gas into the system, during the drying step if the floors are unheated or if the liquid begins to freeze due to evaporative cooling. The vent gas carries heat energy with it.

It is important to obtain a substantially moisture-free environment, before proceeding to the cooling and exposure steps, in accordance with the present invention. Standing water in the chamber, or on the surfaces of the shelves, may act as a barrier and prevent sterilant vapor from effectively contacting the surfaces to be decontaminated. Also, water may cause condensation of the sterilant, thereby diluting the concentration of sterilant vapor and reducing its efficacy or requiring longer kill times. In addition, concentrated condensed sterilant, such as liquid hydrogen peroxide, may degrade or harm the freeze dryer components more readily when compared to the vapor sterilant.

In the system of FIGS. 1 and 2, pressure transducers 22 and 24 are monitored during the drying step. Substantial dryness is indicated by substantially identical pressure transducer readings. Any suitable set of pressure transducers, such as a Piranhi gauge, and an MKS Baritron, can be employed. When the two vacuum readings are equal the chamber will be dry since one transducer senses water vapor and the other does not. It is also contemplated that other known methods for detecting moisture can be employed to signify that the chamber 6 and condenser 2 have been substantially dried.

After the drying step, a leak test is preferably conducted to test for pressure leaks. Any suitable known method may be employed. In the embodiment shown in FIGS. 1 and 2, the vacuum system 16 evacuates the condenser 2, chamber 6, and piping through valves 32 and 38, to about 1 Torr absolute pressure, as determined by pressure transducer 22. Valves 44, 46, and 48 are positioned to evacuate the piping up to valves 52, 50, 54, and 42 which are closed. Then valves 40, 36, 34, 32, 48, 38 are all closed and 30 and 52 are not closed, while pressure transducer 22 monitors the chamber pressure for a predetermined time period. If the leak rate (or pressure rise) is less than a preset value for the tolerable leak level, the method proceeds to the cooling step. Because any residual moisture may also cause the chamber pressure to rise (the vapor pressure of the water is sensed by pressure transducer 22), the exemplified leak test also verifies that the system is dry. Additionally, an automated integrity test in the circuit containing the air filters 58 may be employed, thereby eliminating the need to remove the filters to test their integrity before, or after, the decontamination cycle.

Figure 4:
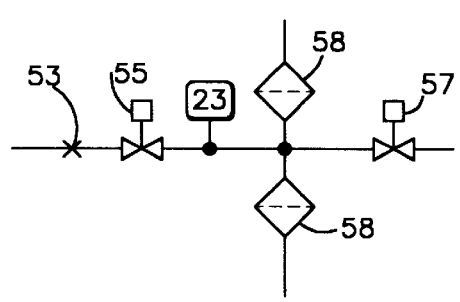
FIG. 4 is a schematic diagram of the automated integrity test used to determine whether there is a leak in the system.

FIG. 4 is a schematic that illustrates this automated integrity test. This test requires an additional pressure sensor 23 and additional valves 55 and 57. Valve 57 is opened to wet both filters 58 with sterile water. Then valve 57 closes and valve 55 opens to draw a slight vacuum between the filters. A restrictor orifice 53 can be used to facilitate drawing the proper vacuum as sensed by pressure transducer 23.

Values 54 and 44 are opened to permit air to flow through the filter toward the vacuum in the piping between filters 58. Pressure transducer 23 monitors the rate of pressure rise in this piping volume when valves 55 and 57 are both closed. The slight pressure differential created by the vacuum is insufficient to draw air through the wet filter 58 at a rate greater than a predetermined value if the integrity of the filters is not compromised.

After the leak test, the cooling step begins. Valves 92 and 94 are opened, and pumps 66, 68, 70, 72, 74, 76, 78, 80, 82, and 86 are controllably operated to cool the chamber 6, shelves 10, and condenser 2 to a substantially uniform temperature lying between about 10° C. and about 40° C., and preferably about 30° C. Heaters 26 and 28 continue to heat the sterilant delivery lines, coupled to the chamber 6 and condenser 2, to about 50° C.

Next, the exposure step begins. Vacuum pump 16 evacuates the chamber 6 and condenser 2 through valves 32 and one or more of valves 40, 36, and 38, to a preselected subatmospheric pressure as measured by pressure transducer 22. The subatmospheric pressure is preferably less than or equal to about 5 Torr, and more preferably about less than or equal to 1 Torr.

Valve 32 is closed, and hydrogen peroxide vapor is introduced through valve 52 into the system from generator 12. Valve 48 is closed to prevent any steam from reaching valve 48, adjacent to the condenser 2, and increasing its temperature.

The chamber 6, shelves 10, and condenser 2 are exposed to the sterilant vapor, preferably hydrogen peroxide vapor, under vacuum, for a period of time sufficient to achieve the desired level of decontamination, which is preferably sterilization. The shelves 10 can be controllably raised and lowered during sterilization to optimally expose all surfaces to the-hydrogen peroxide vapors. Moreover, the means for moving the shelf is contained in an enclosure external to the chamber.

Figure 5:
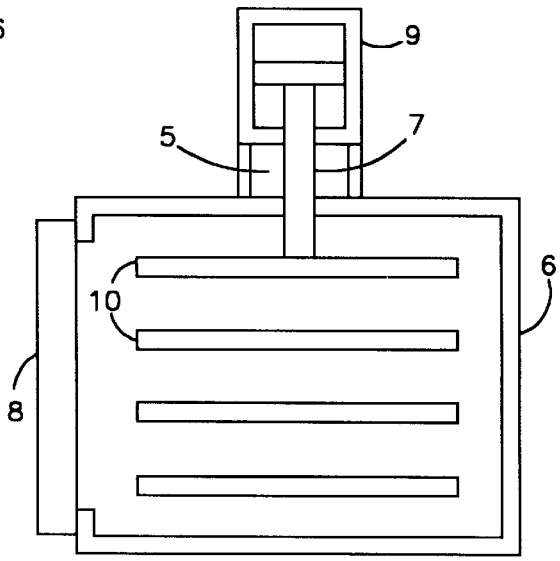
FIG. 5 is a schematic showing a mechanism to raise and lower the chamber shelves by a means external to the chamber.

FIG. 5 is a schematic illustrating a freeze dryer with shelves that can be raised and lowered by an external mechanism, such as a hydraulic cylinder consisting of housing 9 and piston rod 7, and external chamber 5 which can be constructed so that its interior surface can be sterilized along with chamber 6. Then, when the cylinder 7 extends lowering the shelves, it will not contaminate sterile chamber 6. Additional valves and pressure sensors can be utilized to permit chamber 5 to be sterilized independently of chamber 6. The external moving means can be optionally sterilized separately or in the same step when sterilizing the chamber and condenser.

Preferably, the temperature distribution within the chamber 6 and condenser 2, and more preferably, also the shelves 10, is maintained to within plus and minus about three degrees of a setpoint temperature ranging between about 10° C. and about 40° C., during the exposure step.

Also, the exposure step preferably is comprised of sterilization pulses which sequentially introduce sterilant vapor into the chamber 6 and condenser 2, for a predetermined period of time, admit a filtered air flow into the chamber 6 and condenser 2 for another period of time to reach a higher pressure and then reevacuate the chamber 6 prior to repeating the sterilization pulse. Sterilization pulses are usually repeated from about 2 to 32 times until sterilization is obtained. Additional sterilant may be included in the filtered air flow that occurs prior to each re-evacuation, until the desired decontamination is obtained.

A separate sterilization circuit is provided for air filters 58 so that they can be sterilized independently as well as in conjunction with the chamber 6 and condenser 2. This circuit may or may not, include the hardware to accommodate an automated filter integrity test that is illustrated in FIG. 4.

The exposure time period of the individual pulses and the total number pulses needed to achieve sterilization can be determined empirically. Other known sterilization cycles such as a combination vacuum/flow-through method that is employed in commonly owned U.S. Pat. No. 5,492,672, could be employed, disclosure for which is incorporated by reference herewith.

In the system of FIGS. 1 and 2, a preselected amount of sterilant (or sterilant laden air) is admitted into the chamber 6 and condenser 2, through either or both of valves 52 and 54, in a controlled manner. After a first preselected time period air (or sterilant laden air) is again admitted into chamber 6 and condenser 2 through either, or both of, valves 52 and 54 in a controlled manner until the pressure in the chamber 6 and condenser 2 reaches a preselected value, as determined by transducer 22. After a second preselected time period, the chamber 6 and condenser 2 are re-evacuated and the steps of introducing sterilant and air are repeated, until decontamination is complete.

Preferably, air is admitted into the chamber 6 and condenser 2 rapidly, after the first preselected time period to compress the sterilant vapor against the surfaces to be decontaminated, and to compress the sterilant within the deadlegs and other relatively inaccessible areas. This vapor compression method for optimizing sterilization is disclosed in commonly owned application Ser. No. 07/973,372, filed concurrently herewith, and incorporated by reference herein.

Generally, the exposing step is followed by aeration, to remove substantially all sterilant vapor from the freeze dryer, before the chamber door is opened and the freeze dried product removed. Aeration preferably comprises repeatedly evacuating the chamber 6 and condenser 2 and admitting a filtered venting gas (such as air, nitrogen, and helium) to reach a predetermined pressure, until the sterilant vapor concentration in the chamber 6 and condenser 2 reaches a preselected value, to be determined empirically. The chamber 6, condenser 2, and shelves 10 may be warmed to a temperature between about 40° C. and 60° C., to shorten the duration of the aeration step.

This elevated temperature during aeration increases the rate at which the residual hydrogen peroxide vapor decomposes into water vapor and oxygen. The addition of energy, other than thermal, would also be anticipated to increase the decomposition rate of residuals and decrease the aeration time. Examples of other sources of energy would include infrared, ultraviolet, microwave, radio frequency (RF) and ultrasonic.

In the system of FIGS. 1 and 2 during aeration, valves 88 and 90 are opened, and pumps 66, 68, 70, 72, 74, 76, 78, 80,

82, and 84 are controllably operated to warm the chamber 6, shelves 10, condenser 2 and condenser coils to about 50° C. Heaters 26 and 28 continue to heat the sterilant delivery lines to about 50° C. Vacuum system 16 evacuates the chamber 6 and condenser 2 through valve 32 and one, or more, of valves 36, 40, and 38 to a pre-selected pressure as determined by transducer 22. Then, valve 32 is closed and valve 54 is opened to admit filtered air, until the pressure reaches a higher level. This procedure is repeated until the residual sterilant concentration drops below a specified value, such as less than about 1 ppm. Subsequently, the chamber 6 and condenser 2 are vented to atmospheric pressure so that the access chamber door can be opened, prior to loading the chamber for the next freeze drying cycle.

While the invention is susceptible to various modifications and alternative forms, the preferred embodiments have been described herein in detail. It is to be understood, however, that it is not intended to limit the invention to the specific forms disclosed. On the contrary, it is intended to cover all modifications and alternative forms falling within the spirit and scope of the invention.

For example, in the illustrated examples, the source of vapor sterilant is external to the chamber 6. It is also contemplated that the vapor sterilant can be generated within the chamber.

FIG. 3

The system in FIG. 3, includes a condenser 120, refrigerator coils 121 of cooling condenser 120, a chamber 122 having access door 123 and shelves 124.

An overflow collection means can be installed on the chamber in this and other embodiments in case main valve 113 inadvertently permits water to flow from the condenser into the chamber. This would prevent the chamber from flooding and possibly forcing the chamber door seal to dislodge and leak.

In FIG. 3, the heat transfer fluid is recirculated by Pumps 100 and 101 through heat exchangers 102 (cooler) and 103 (heater) and then through the chamber jacket 125, chamber shelves 124 and condenser jacket 126. Valves 104, 105 and 115 through 119 control the circuits through which the fluid passes. Heat is added to the recirculating fluid by heat exchanger 102 or removed from the recirculated fluid by heat exchanger 103 as required during the process.

The condenser coils are cooled, but not warmed, by refrigeration systems. Compressors 106 and 107 compress the recirculating refrigerant, pass it through condensers 108 and 109 where heat energy is removed and finally push it through expansion valves 110 and 111 just as it enters the refrigeration coils. As the refrigerant expands, it cools the condenser coils.

An expansion tank 114 is utilized in recirculating heat transfer fluid illustrated in the heating/cooling embodiment shown in FIG. 3. An expansion tank is likewise required, but not shown, for the embodiment depicted in FIG. 2.

EXAMPLE I

Preparation of Freeze Dryer Components

The condenser is isolated from the chamber and water is flooded throughout the condenser. Steam is continuously admitted to heat the water to 50° C. The steam is controllably admitted thereafter to maintain the water temperature at 50° C. In turn, the chamber, shelves, condenser and condenser coils are heated to 50° C. via heat exchangers. The piping is heated by heaters to 50° C. After a sufficient time to thoroughly defrost the components, condenser and chamber are drained by gravity.

All remaining water is withdrawn from the drain lines when air is drawn into the chamber and condenser and out through the drain lines. The chamber and condenser are then deeply evacuated to less than 10 Torr and drying continues until all the remaining water in the chamber, condenser, and piping has evaporated. When the measurements taken by a Piranhi gauge and MKS capacitance vacuum gauge are identical, the leak dry phase is completed.

A vacuum pump evacuates the condenser, chamber and piping to 1 Torr absolute pressure. A pressure transducer monitors the chamber pressure for a predetermined time period, and if the leak rate is less than a preset value, the cycle continues. Chamber, condenser and shelves are then cooled to 30° C., while heaters continue to heat the piping to 50° C.

Sterilization of Freeze Dryer Components

A vacuum pump evacuates the chamber and condenser (whose combined volume is 154 cubic feet) to a pre-injection pressure that is less than or equal to 1 Torr. A hydrogen peroxide generator utilizing the "High Capacity Multicomponent Liquid Vaporizer" described in U.S. Pat. No. 5,068,087 introduces 12.2 grams of hydrogen peroxide vapor (along with 27.2 grams of water vapor) into the chamber and condenser to produce a hydrogen peroxide vapor concentration of 2.79 mg/liter. This concentration was obtained from Table II in U.S. Pat. No. 4,956,145 entitled "Optimum Hydrogen Peroxide Sterilization Method" for a vapor temperature of 30° C. and a relative humidity (deep vacuum) of zero percent.

After a 4 minute sterilize hold time, sterile filtered air is admitted into the chamber and condenser until the pressure reaches 165 Torr. After an additional 2 minute hold time period, the vacuum pump evacuates the chamber and condenser as the above series of sterilization steps are repeated. Each series of steps comprises one sterilization pulse. The sterilize phase consists of between 2 and 32 sterilization pulses.

Aeration of Freeze Dryer Components

The chamber, shelves, condenser and condenser coils are heated to 50° C. by heat exchangers. Heaters are used to heat the piping to 50° C. also. A vacuum pump then evacuates the chamber and condenser to a preselected pressure, of 5 Torr. Venting gas such as air, dry air, nitrogen or helium are admitted until the pressure reaches a pre-selected pressure, of 650 Torr. Aeration pulses are continued for a specified number of times or until the residual hydrogen peroxide vapor concentration is below 1 ppm. The chamber and condenser are then vented to atmospheric pressure so the chamber access door can be opened.

While this invention has been described in connection with preferred embodiments, it is not intended to limit the scope of the invention to particular embodiments set forth, but, to the contrary, it is intended to cover such alternatives, modifications, and equivalents as may be included within the spirit and scope of the invention as defined by the appended claims.

EXAMPLE II

Preparation of Freeze Dryer Components

The condenser, which is located directly below the chamber, is continuously flooded with 50° C. water. An overflow tube within the condenser drains off excess water continuously without flooding the chamber. This flooding continues until the temperature within the condenser equals 48° C.

The chamber shelves are controllably heated to 48° C. by the recirculating heat transfer fluid and the chamber floor and walls are controllably heated by electric blanket heaters to 48° C. while the condenser is defrosting.

The main drain valve located in the bottom of the condenser is opened so that the water will drain out due to gravity. Sterile filtered compressed air is admitted into the chamber at 1 psig (maximum) pressure to displace any water remaining in the drain lines.

All valves except the one to the vacuum line in the top of the condenser are closed. A dry pulse begins when the vacuum pump evacuates the chamber to 4 Torr. Sterile filtered air is then admitted until the pressure in the chamber reaches 600 Torr completing the dry pulse. These dry pulses are repeated 12 times completely drying out the chamber and condenser.

The chamber and condenser are evacuated to 1 Torr and all valves closed. After a thirty second delay, the absolute pressure within the chamber is monitored for 10 minutes. If the pressure in the chamber does not rise more than 200 microns, the cycle continues. The chamber shelves are controllably cooled to 40° C. during the leak test. The chamber floor, walls and condenser have also cooled to about 40° C. by this time and are controlled at this temperature.

Sterilization of Freeze Dryer Components

A vacuum pump evacuates the chamber and condenser (combined volume of 5.2 cubic feet) to a pre-injection pressure that is less than or equal to 1 Torr. A hydrogen peroxide generator utilizing the "Method of Vaporizing Multicomponent Liquids" described in U.S. Pat. No. 4,642,165 introduces 0.75 grams of hydrogen peroxide vapor (along with 1.67 grams of water vapor) into the chamber and condenser to produce a hydrogen peroxide vapor concentration of 5.03 gm/liter. This concentration was obtained from Table II in U.S. Pat. No. 4,956,145 entitled "Optimum Hydrogen Peroxide Sterilization Method" for a vapor temperature of 40° C. and a relative humidity (deep vacuum) of zero percent.

After a 3 minute sterilize hold time, sterile filtered air is admitted into the chamber and condenser until the pressure reaches 150 Torr. After an additional 1½ minute hold time period, the vacuum pump evacuates the chamber and condenser as the above series of sterilization steps are repeated. Each series of steps comprises one sterilization pulse. The sterilize phase consists of between 2 and 32 sterilization pulses.

What is claimed is:

1. A method for decontaminating a freeze dryer after a freeze drying cycle has been completed, the condenser has been defrosted and the chamber has been rinsed with water, comprising the steps of:
   a) providing a freeze dryer comprising a chamber and a condenser fluidly connected to each other and to a source of sterilant vapor, wherein the chamber comprises a chamber floor having a first drain port fluidly connected to a first drain line, and the condenser comprises a condenser floor having a second drain port fluidly connected to a second drain line;
   b) providing a vacuum pump fluidly coupled to each of the drain lines downstream of their drain ports;
   c) operating the vacuum pump for a period of time sufficient to evacuate substantially all moisture remaining in the chamber through the first drain port and first drain line and in the condenser through the second drain port and second drain line, while heating the chamber and the condenser at a temperature sufficient to prevent freezing of substantially all of the remaining moisture during the evacuation of the chamber and the condenser;
   d) after the simultaneous evacuating and heating of the chamber and the condenser, cooling the chamber and the condenser for a period of time sufficient to lower the temperature in the chamber and the condenser to between about 10° C. and about 40° C.; and
   e) exposing the chamber and the condenser to a sterilant vapor comprising hydrogen peroxide vapor and water vapor, at a subatmospheric pressure and at a temperature between about 10° C. and about 40° C. for a period of time sufficient to achieve a predetermined level of decontamination.

2. The method of claim 1, wherein the step of heating comprises direct heating of the chamber floor and the condenser floor.

3. The method of claim 1, wherein the step of heating the chamber floor and the condenser floor comprises admitting vent gas into the chamber and the condenser.

4. The method of claim 1, wherein the chamber has a shelf and the step of heating comprises direct heating of the chamber shelf.

5. The method of claim 1, wherein the predetermined level of decontamination is sterilization.

6. The method of claim 1, wherein the step of exposing the chamber and the condenser to the sterilant further comprises maintaining the temperature within the chamber and the condenser to within plus and minus about three degrees of a temperature set point ranging between about 10° C. and about 40° C.

7. The method of claim 1, which further comprises the step of aerating the chamber and the condenser after step (e).

8. The method of claim 1, wherein the pressure in the chamber and the condenser during exposure to the sterilant is from between about 5 Torr to about 200 Torr.

9. The method of claim 1, wherein the temperature during the heating step is maintained at between about 40° C. and about 60° C.

10. The method of claim 9, wherein the temperature during the heating step is maintained at about 50° C.

11. The method of claim 1, which further comprises the steps of: providing movable shelves within the chamber; locating shelf-moving means in an enclosure external to the chamber; and exposing the external enclosure to the sterilant vapor.

12. Apparatus for decontaminating a freeze dryer after a freeze drying cycle has been completed, the condenser has been defrosted and the chamber has been rinsed with water comprising:
   a) a freeze dryer comprising a chamber and a condenser fluidly connected to each other and to a source of sterilant vapor, wherein said chamber comprises a chamber floor having a first drain port fluidly connected to a first drain line, and said condenser comprises a condenser floor having a second drain port fluidly connected to a second drain line;
   b) a vacuum pump fluidly coupled to each of the drain lines for evacuating the chamber and the condenser to remove substantially all remaining moisture from the chamber through the first drain port and first drain line and from the condenser through the second drain port and second drain line;

c) means for controllably heating the chamber and the condenser to maintain a temperature sufficient to prevent freezing of substantially all remaining moisture in the chamber and the condenser during the evacuation of the chamber and the condenser; and d) means for controllably cooling the chamber and the condenser to a temperature between about 10° C. and about 40° C. after the simultaneous evacuation and heating of the chamber and the condenser;

e) means for introducing a sterilant vapor comprising hydrogen peroxide vapor and water vapor into the cooled chamber and the cooled condenser at a subatmospheric pressure for a time period sufficient to obtain a predetermined level of decontamination.

13. The apparatus of claim 12, wherein the heating means comprises means for directly and controllably heating the chamber floor and the condenser floor.

14. The apparatus of claim 12, wherein the chamber further comprises a chamber shelf, and the heating means comprises means for directly and controllably heating the chamber shelf.

15. The apparatus of claim 12, wherein the heating means comprises means for admitting vent gas into the chamber and the condenser.

* * * * *